United States Patent [19]

Peters et al.

[11] Patent Number: 5,744,146
[45] Date of Patent: Apr. 28, 1998

[54] ANHYDROUS DELIVERY VEHICLE FOR COSMETIC INGREDIENTS

[76] Inventors: Kimberly T. Peters, 347 Set Point Dr., Piney Flats, Tenn. 37686; Paul A. Rundquist, 2601N John B. Dennis, #1409, Kingsport, Tenn. 37660; John J. Hiller, 5332 Foxfire Pl., Kingsport, Tenn. 37664

[21] Appl. No.: 638,720

[22] Filed: Apr. 29, 1996

Related U.S. Application Data

[63] Continuation of Ser. No. 398,828, Mar. 6, 1995, abandoned.

[51] Int. Cl.⁶ .................... A61K 7/00; A61K 7/48
[52] U.S. Cl. ........................ 424/401; 424/DIG. 5
[58] Field of Search .................. 424/401, DIG. 5

[56] References Cited

U.S. PATENT DOCUMENTS

| | | | |
|---|---|---|---|
| 4,695,452 | 9/1987 | Gannis et al. | 424/59 |
| 4,759,924 | 7/1988 | Luebbe et al. | 424/42 |
| 4,919,934 | 4/1990 | Deckner et al. | 424/401 |
| 4,950,475 | 8/1990 | Vishnupad et al. | 424/83 |
| 5,194,262 | 3/1993 | Goldberg et al. | 424/401 |
| 5,209,925 | 5/1993 | Lindauer et al. | 424/73 |

OTHER PUBLICATIONS

Dweck, A.C., "The sweating of lipsticks", *Cosmetics & Toiletries*, 96, 1981, pp. 29–32.

*Primary Examiner*—Sally Gardner-Lane
*Attorney, Agent, or Firm*—Andre B. Griffis; Harry J. Gwinnell

[57] ABSTRACT

This invention relates to an anhydrous delivery vehicle for applying cosmetic or functional active ingredients to human skin. The anhydrous delivery vehicle contains 5 to 30 weight percent of a high-melting wax, 5 to 30 weight percent of an acetylated monoglyceride, 5 to 60 weight percent of petrolatum, 0.1 to 30 weight percent of a fatty alcohol having 8 to 22 carbon atoms, and a cosmetic or functional active material.

5 Claims, No Drawings

ANHYDROUS DELIVERY VEHICLE FOR COSMETIC INGREDIENTS

This is a continuation of application Ser. No. 08/398,828 filed on Mar. 6, 1995, now abandoned.

FIELD OF THE INVENTION

This invention relates to an anhydrous delivery vehicle for applying cosmetic or functional active ingredients to human skin.

BACKGROUND OF THE INVENTION

Stick formulations containing pigments dispersed in wax and oil binders have been used to deliver cosmetic ingredients to skin since ancient times. Lipsticks and colored makeup sticks are the oldest form of cosmetic sticks. Stick formulations can be classified into four primary types: alcohol gels, polyol gels, alcohol-wax gels, and wax-fat-oil sticks.

Many deodorant stick systems are based on alcohol gelled with sodium stearate. A major drawback of this kind of stick is that the alcohol has a tendency to evaporate which changes the properties of the stick over time. Polyols such as glycerol and propylene glycol have been used to reduce the rate of alcohol evaporation. Unfortunately, common alcohol-stearate sticks are incompatible with some active ingredients such as the common aluminum antiperspirant salts. Antiperspirant sticks, for reasons of stability with these salts, are usually based on either a cetyl-stearyl alcohol or a fatty amide-wax base.

Lipsticks are examples of anhydrous stick formulations of the wax-fat-oil type, consisting of waxes for structure, pigments for color, and castor oil or other oils for pigment dispersing and emolliency. Such wax/oil sticks are often ozokerite/mineral oil or carnauba/castor oil compositions. Unless the formulation is ideally balanced, syneresis (i.e., separation of liquid from the solid matrix) can be a problem. Syneresis has been linked to structural changes (phase changes) in the wax matrix with time, and, hence, is related to the compatibility of the wax used with the rest of the components in the formulation (A. C. Dweck, Cosmet. Toilet. 96, 29 (1981)). Dweck reports cases where formulations using synthetic straight carbon chain waxes became so brittle with time as to fall apart within a few hours of preparation.

Specific formulations of cosmetic sticks can be found in the cosmetic and patent literature for various uses such as moisturizers, perfume sticks, sun screen sticks, antiperspirants, deodorants, and pigmented sticks such as lipsticks, blushes, or eye shadow. Formulations for cosmetic sticks vary from compressed powders and gel sticks to emulsion sticks and wax sticks. A particularly common form of cosmetic stick utilizes a gel such as a soap gel or soap/alcohol gel. U.S. Pat. No. 4,759,924 discloses a transparent soap gel cosmetic stick composition which contains a polyhydric aliphatic alcohol, a hydroalcoholic soluble emollient, water and soap. The problem with alcohol-stearate gel sticks, however, is that they are not compatible with many active ingredients. Moreover, alcohol-stearate gel sticks require elaborate packaging for dispensing and preventing the stick from drying out.

U.S. Pat. No. 4,950,475 discloses an emulsion gel cosmetic stick composition containing a water dissipatable polymer, humectants, emollients, water and emulsifier. Surfactants are required in emulsion sticks to incorporate nonpolar, water-immiscible ingredients into the stick. The surfactants, however, decrease the water-resistance of such formulations on the skin.

U.S. Pat. No. 4,695,452 discloses a process for preparing cosmetic stick formulations containing an acetylated monoglyceride, beeswax and isopropyl myristate. Isopropyl myristate is a low viscosity ester which is considered oil-free. The cosmetic stick formulation has a high coefficient of friction which produces a massaging action upon application to skin.

Moisturizing is an important attribute of many cosmetic formulations, including stick formulations. Humectants and emollients are common ingredients in stick formulations. Humectants function as moisturizers by binding water to the skin. This mode of action is in contrast to occlusive moisturizing which functions by retarding the rate of water transpiration through the skin. An emollient is defined as any material which softens the skin, and since dried, scaly skin is inherently rough, both humectant and occlusive moisturizing compounds are considered emollients. In general, occlusive moisturizers are quite effective but often not cosmetically acceptable. For example, petrolatum is highly occlussive but is an oily substance that leaves behind an unacceptable greasy film.

Accordingly what is needed is a stable anhydrous cosmetic composition which delivers a high concentration of hydrophobic cosmetic or functional active ingredients to the skin as a non-oily, non-greasy film which is aesthetically pleasing.

SUMMARY OF THE INVENTION

This invention relates to an anhydrous delivery vehicle for applying cosmetic or functional active ingredients to human skin, said anhydrous delivery vehicle comprising a blend of:

(A) 5 to 30 weight percent of a wax having a melting point of greater than 50° C. and a weight average molecular weight of less than 15,000;

(B) 5 to 30 weight percent of an acetylated monoglyceride;

(C) 5 to 60 weight percent of petrolatum having a specific gravity between 0.815 and 0.880 at 60° C., and a melting range between 38° and 60° C.;

(D) 0.1 to 30 weight percent of a fatty alcohol having 8 to 22 carbon atoms; and (E) 0.05 to 50 weight percent of a cosmetic or functional active material selected from the group consisting of emollients, sunscreens, vitamins, humectants, botanicals, insect repellents, skin protectants, antiperspirants, bactericides, antiseptics, moisturizers, antioxidants, buffers, pigments, colorants, dyes, fragrances, titanium dioxide, talc, and combinations thereof.

DESCRIPTION OF THE INVENTION

The anhydrous delivery vehicle of the present invention contains a blend of at least five ingredients. The anhydrous delivery vehicle contains a wax, an acetylated monoglyceride, petrolatum, a fatty alcohol, and a cosmetic or functional active material. The anhydrous delivery vehicle is preferably in the form of a stick composition which is used to apply various cosmetic or functional active ingredients to skin.

Component (A) is a wax having a melting point of greater than 50° C. and a weight average molecular weight of less than 15,000. Preferably, the wax has a melting point of greater than 100° C. and a weight average molecular weight of less than 10,000. The wax provides the basic structure of the anhydrous delivery vehicle. The hardness and wear rate of an anhydrous delivery vehicle can be changed by varying type or amount of wax in the formulation. The wax is present in an amount of 5 to 30 weight percent of the formulation, preferably 10 to 20 weight percent. Waxes suitable for use in the present invention include, but are not limited to, polyethylene wax, petroleum waxes, paraffin, ozokerite, carnauba, beeswax, candelilla, and microcrystalline waxes. Mixtures of waxes may also be used. Preferably, the wax is a synthetic polyethylene wax such as EPOLENE N-21 having a weight average molecular weight of 6,500, or an oxidized polyethylene such as EPOLENE E-20 having a weight average molecular weight of 7,500. The EPOLENE type waxes are available from Eastman Chemical Company.

Component (B) is an acetylated monoglyceride which is present in an amount of 5 to 30 weight percent, preferably 10 to 20 weight percent, of the anhydrous delivery vehicle formulation. The acetylated monoglyceride may be either mono or di acetylated or a mixture thereof. The acetylated monoglyceride serves as a solvent for the wax and other materials in the anhydrous delivery vehicle. The acetylated monoglyceride acts also as an emollient and occlusive. In the case where the anhydrous delivery vehicle is used as a cosmetic stick, the acetylated monoglyceride acts to plasticize the stick to give it more drag on the skin and to decrease the greasy feel of the stick especially when high levels of petrolatum are used in the formulation.

Preferred acetylated monoglycerides are MYVACET 7-07, MYVACET 9-45, and MYVACET 5-07 which are available from Eastman Chemical Company. MYVACET 7-07 is a waxy solid at room temperature and has a 70% degree of acetylation and an iodine value of 5 or less. MYVACET 9-45 is a fully acetylated monoglyceride, is a liquid at room temperature and has a 96% minimum degree of acetylation and an iodine value between 43 and 53. MYVACET 5-07 is a waxy solid at room temperature and has a 50% degree of acetylation and an iodine value of 5 or less. The fat source used in preparing the acetylated monoglyceride as well as the degree of acetylation has an effect on the aesthetic properties of the formulated cosmetic product.

The third component of the anhydrous delivery vehicle formulation, component (C), is petrolatum. Petrolatum is a purified mixture of semisolid hydrocarbons derived by fractional distillation of still residues from steam distillation of paraffin-base petroleum, or from steam-reduced crude oils from which the light fractions have been removed. Petrolatum has a specific gravity between 0.815 and 0.880 at 60° C., and a melting range between 38° and 60° C. The petrolatum may contain a suitable stabilizer such as food-grade butylated hydroxy toluene. The nature of the petrolatum is not particularly critical, so long as the petrolatum is white, amber, or red. White petrolatum is a purified mixture of semisolid hydrocarbons obtained from petroleum, and wholly or nearly decolorized. Amber petrolatum is a medium consistency petrolatum. Red petrolatum is a minimally refined variety of petrolatum. Petrolatum is present in an amount of 5 to 60 weight percent, preferrably 15 to 35 weight percent of the formulation. The petrolatum serves as a solvent for cosmetic or functional active materials and contributes to the occlusive nature of stick compositions on skin.

Component (D) is a fatty alcohol having 8 to 22 carbon atoms. The fatty alcohol may be in the form of a liquid or a solid. Preferably, the fatty alcohol has 12 to 18 carbon atoms. Fatty alcohols with less than 8 carbon atoms are too volatile to be useful in the anhydrous delivery vehicle formulations of the present invention. The fatty alcohol is present in the anhydrous delivery formulation in an amount of 0.1 to 30 weight percent, preferably 10 to 20 weight percent. The fatty alcohol functions as an emollient and aids in the dispersion of cosmetic or functional active materials. Fatty alcohols suitable for use in the present invention include saturated alcohols such as octyl, decyl, lauryl, myristyl, cetyl, stearyl, and cetearyl. Fatty alcohols suitable for use in the present invention also include unsaturated alcohols such as oleyl, linoleyl, and linolenyl. In the case where an unsaturated fatty alcohol is used, an antioxidant is preferably included to stabilize the unsaturated fatty alcohol. A preferred fatty alcohol is cetearyl alcohol which is a blend of cetyl and stearyl alcohols.

Component (E) is a cosmetic or pharmaceutically active material. Suitable cosmetic or pharmaceutically active materials for use in the anhydrous delivery vehicle of the present invention are: emollients, sunscreens, vitamins, humectants, botanicals, insect repellents, skin protectants, antiperspirants, bactericides, antiseptics, moisturizers, antioxidants, fragrances, pigments, colorants, dyes, titanium dioxide, talc, and the like. The cosmetic or pharmaceutically active materials are present in an amount of 0.05 to 50 weight percent, preferably 0.1 to 25 weight percent, of the total anhydrous delivery vehicle formulation. Combinations of cosmetic and pharmaceutically active materials can also be employed in the anhydrous delivery vehicles of the present invention.

Suitable humectants include:
(1) propylene glycol, dipropylene glycol, tripropylene glycol
(2) butylene glycol (1,4+1,3)
(3) polyoxyethylene
(4) polyethylene glycol
(5) hexylene glycol
(6) urea, and
(7) ethoxydiglycol.

Suitable emollients include:
(1) mineral oil
(2) isopropyl palmitate laurate, myristate, etc. (other esters)
(3) squalene, squalene
(4) glycol esters (butyl stearate, etc.)
(5) lanolin and derivatives
(6) cholesterol
(7) coconut oil, avocado oil, olive oil, other vegetable oils including cocoa butter, corn oil
(8) silicones
(9) mink oil, tallow, other animal fats and oils, and
(10) ethoxylated alcohols, proproxylated alcohols and EO/PO alcohols.

The anhydrous delivery vehicle may contain a combination of antioxidant compounds. Preferably, one such antioxidant component is vitamin E (dl-alpha-tocopherol). A second antioxidant component is ascorbyl palmitate (the palmitic acid of vitamin C) is useful as a free radical scavenger. The antioxidation characteristic of the combination of vitamin E with ascorbyl palmitate has been sugested to reduce the rate of aging of human skin.

The formulations of the present invention are prepared by adding components (A) through (E) to a suitable vessel and heating while stirring until a homogeneous melt is obtained. The composition is cooled to slightly above its solidification point, poured into a container and allowed to solidify. Optionally, heat sensitive ingredients may be added just prior to pouring to reduce the time such components are subjected to heat. If pigments are to be used, they may be dispersed into the petrolatum, component (C), and acetylated monoglyceride, component (B), before being combined with components (A), (D) and (E). High shear mixing may be required to adequately disperse the pigments.

In addition to components (A) through (E), the formulations of the present invention may also contain fillers and other additives commonly used in cosmetic formulations. Mixtures of additives may also be used. Such additives, their amounts, and their use are well known in the art.

A particularly advantageous utilization of the anhydrous delivery vehicle formulations of the present invention is in the form of a stick. In the case of a stick, the wax, component (A), provides structure to the stick. If the level of wax falls below a certain amount, the stick loses its integrity. The lowest level of wax used in the formulation is dependent on the amount: of petrolatum, component (C), and the amount of the cosmetic or functional active material, component (E), which is incorporated into the stick. For high amounts of cosmetic or functional active material, a relatively high amount of wax is needed. Conversely, for low amounts of cosmetic or functional active material, a lower amount of wax can be used.

Preferably, in stick formulations, the weight ratio of wax to acetylated monoglyceride is 1:1. Loading of oil material up to 25% can be accomplished without severely softening the stick by adjusting the level of wax. The tensile properties of wax/acetylated monoglyceride blends are closely related to the properties of the wax used. By adjusting the level and type of wax, sticks with a particular set of physical properties can be formulated.

The materials and testing procedures used for the results shown herein are as follows:

DEET is N,N'-Diethyl-m-toluamide, an insect repellant which is available from Hoechst Celanese.

ESCALOL 557 is ethylhexyl methoxycinnamate which is available from ISP Van Dyk Inc.

TENOX GT-2 is an antioxidant consisting of natural tocopherols derived from vegetable oilseeds which is available from Eastman Chemical Company.

Lanette Wax O is cetearyl alcohol which is available from Henkel.

The process of the present invention will be further illustrated by a consideration of the following examples, which are intended to be exemplary of the invention. All parts and percentages in the examples are on a weight basis unless otherwise stated.

EXAMPLES 1–7

Various anhydrous stick formulations were prepared by combining the components, as listed for each example in Table I, in a suitable vessel and heating with stirring until a homogeneous melt was obtained. The homogeneous melt was poured into a mold at a temperature just above its solidification point.

In Example 4, which contains zinc oxide, the zinc oxide was first dispersed into a mixture of petrolatum, Myvacet 7-07 and mineral oil using a high shear mixer before being combined with the other components. In Examples 5 and 6 which contain fragrance oils and flavor oils respectively, the oils were the last components added, just prior to pouring into the mold.

The formulations prepared in Examples 1–7 were homogeneous, waxy, non-greasy solids which rubbed easily onto the skin. Example 5, a fragrance stick, had a slightly oily feel due to the use of Myvacet 9-45, a fully acetylated monoglyceride prepared from an oil having some degree of unsaturation.

TABLE I

Examples of Various Anhydrous Stick Formulations

| Component Type | 1 | 2 | 3 | 4 | 5 | 6 | 7 |
|---|---|---|---|---|---|---|---|
| (A) Wax: | | | | | | | |
| Petroleum | | 12.9 | | 20.0 | | | |
| Candelilla | | | | | 6.0 | | |
| Paraffin | | | | | 4.0 | | |
| Microcrystalline | | | | | 2.0 | | |
| Beeswax | | | | | 4.0 | | |
| Epolene N-21 | 15.5 | | 15.5 | | | | 13.0 |
| Epolene E-10 | | | | 14.0 | | | |
| (B) Acetylated Monoglyceride: | | | | | | | |
| Myvacet 7-07 | 14.0 | 19.4 | 14.0 | 21.0 | | 15.0 | 19.3 |
| Myvacet 9-45 | | | | | 15.0 | | |
| (C) Petrolatum: | | | | | | | |
| Amber | 34.0 | 34.0 | 34.0 | | | 34.0 | 34.0 |
| White | | | | 15.0 | 25.0 | | |
| (D) Fatty Alcohol: | | | | | | | |
| Cetyl Alcohol | | | | | | 18.0 | |
| Lanette Wax O | 17.2 | 17.2 | 17.2 | 10.0 | 20.0 | | 17.2 |
| (E) Functional active Ingredient: | | | | | | | |
| Mineral Oil | 15.5 | 10.5 | 10.1 | 20.0 | 10.0 | 10.0 | 11.5 |
| Dimethicone | 2.1 | | | | 2.0 | | |
| Methyl Salicylate | | 5.0 | | | | | |
| Menthol | | 1.0 | | | | | |
| DEET | | | | | | | 5.0 |
| Escalol 557 | | | 7.5 | | | | |
| Tenox GT-2 | 1.7 | | 1.7 | | | | |
| Zinc Oxide | | | | 20.0 | | | |
| Fragrance Oil | | | | | 8.0 | | |
| Flavor Oil | | | | | | 2.0 | |
| Cocoa Butter | | | | | | 5.0 | |

The results in Table I clearly show that many different types of cosmetic or functional active ingredients are compatible in the anhydrous delivery vehicle formulations of the present invention.

EXAMPLE 8

Three stick formulations were prepared according to the formulation of Example 1, except that the type of acetylated monoglyceride, component (B), was varied. The formulations were prepared by heating and mixing the components to a homogeneous melt. The homogeneous melt was poured into cylinder molds which consisted of an aluminum tube with a one inch inner diameter and two inches in length resting on a sheet of Teflon coated foil. The mixture was poured to a depth of one inch in the mold.

After cooling, the skin feel, payoff and penetration (hardness) of the sticks was determined.

Skin feel was evaluated qualitatively as the molded stick was applied to skin.

Payoff was determined as follows: A one inch diameter circular molded stick was cut to a height of 1.5 cm using a razor blade. The mold was placed in an aluminum tube which was suspended vertically a short distance above a counter top such that the fresh cut was face down on a strip of paper of known weight which was two inch wide and 12 inches long. A plunger consisting of an aluminum cylinder one inch in diameter and 2.25 inches in length was placed on top of the molded stick. Brass weights are applied to the top of the plunger such that the total weight applied to the top of the molded stick was 400 grams. The paper was drawn slowly from under the stick. The strip of paper was re-weighed and the payoff was recorded as the amount of the stick which deposited on the paper.

Hardness was measured as the distance in millimeters an awl penetrates the stick under an applied weight.

The setup was determined in a manner similar to that for payoff except the aluminum tube was mounted vertically such that it was centered over the point of a vertically held awl with the tip of the awl in the horizontal plane formed by the bottom of the cylinder. A spatula was placed between the tip of the awl and the bottom of the cylinder. The molded stick was placed in the cylinder such that it rested on the spatula at the bottom of the cylinder. The plunger was placed on top of the cylinder and weights were placed on top of the plunger such that the total weight applied to the top of the stick was 138 grams. The distance from the top of the cylinder to the top of the plunger was measured with a micrometer, then the spatula was removed so that the molded stick was forced down onto the tip of the awl by the weight of the plunger and weights. After a period of 30 seconds, the distance from the top of the cylinder to the top of the plunger was measured again. The difference between the two measurements was the penetration depth of the awl into the molded stick. The test results are summarized in Table II.

TABLE II

Properties of Sticks with Various Acetylated Monoglycerides

| Acetylated Monoglyceride | Skin Feel | Penetration (mm) | Payoff (mg) |
|---|---|---|---|
| MYVACET 9-45 | oily | 4.0 ± 0.7 | 24.7 ± 2.6 |
| MYVACET 7-07 | non-oily | 3.2 ± 0.7 | 18.3 ± 2.6 |
| MYVACET 5-05 | non-oily | 3.3 ± 0.7 | 18.7 ± 2.6 |

The ranges represent 95% confidence intervals.

The results in Table II show that the fully acetylated monoglyceride, Myvacet 9-45 made the stick feel slightly more oily and resulted in a slightly higher payoff than sticks prepared with mono or diacetylated monoglycerides. The test results, however, do not indicate any difference in penetration or hardness between the sticks. The higher the penetration value, the softer the stick.

EXAMPLE 9

Two stick formulations were prepared according to the formulation of Example 1, except that the type of wax, component (A), was varied. The stick compositions were poured into cylinder molds as described in Example 8. After cooling, the skin feel, payoff and hardness of the sticks was determined according to the procedure in Example 8. The test results are summarized in Table III.

TABLE III

Properties of Sticks with Various Waxes

| Wax Type | Skin Feel | Hardness (mm) | Payoff (mg) |
|---|---|---|---|
| Epolene N-21 | non greasy | 3.40 ± 0.32 | 17.2 ± 2.8 |
| Epolene E-20 | oily | 4.28 ± 0.51 | 48.8 ± 3.1 |

The ranges represent 95% confidence intervals.

The results in Table III clearly show that the use of an oxidized wax in the stick formulation results in a softer stick with a more oily skin feel and a higher wear rate than a stick formulation containing a non-oxidized wax.

EXAMPLE 10

This example demonstrates the durability of a film formed from a stick composition deposited onto the skin.

The stick composition of Example 5 in which the cosmetic ingredient was a fragrance oil was applied to the back of a persons right hand and rubbed in. The stick composition was not applied to the persons left hand. Both hands were washed with soap and warm water, and patted dry after each washing. The fragrance was detectable on the persons right hand even after four washings.

EXAMPLE 11

This example illustrates the occlusivity of the film formed from the stick formulation prepared in Example 1.

Occlusivity of films was determined by measuring the rate at which a drop of water wicked into Whatman 40 ashless filter paper treated with a fixed amount of the stick formulation. The water was delivered as drops of ca. 0.02 grams each at ambient temperature and humidity via a controlled volume pipette. The time required for the drop to completely disappear into the filter paper sheet following deposition onto the paper is defined as the wicking time. Untreated filter paper wicks water faster than could be measured by a stopwatch. In contrast, water drops placed on filter paper treated with an occlusive material may take minutes to completely wick.

The stick formulation prepared in Example 1 was compared with pure petroleum jelly, which is generally accepted to be a highly occlusive material, and Nivea Creme® which is an emulsion formula which is manufactured by Beiersdorf, Inc. Each test filter paper was prepared by placing a fixed amount (ca. 0.03 grams) of the occlusive test material to be evaluated in the center of the paper, then spreading it out with a finger until ca. 4.9 square cm of area has been treated and appeared homogeneous. The samples were set aside for 30 minutes.

A controlled drop of water was placed in the center of each treated area, and the time for the drop of fluid to decrease in size until equal to the plane of the paper was measured. Five runs of each sample were tested, and the time to wick (in seconds) and the standard deviation of the five measurements was determined. Each sample was then remeasured in the same manner after ca. five hours. The averages and standard deviations for each of the test materials is summarized in Table IV.

TABLE IV

| Sample | Time to Completely Wick (sec) | |
|---|---|---|
| | After 30 min | After 5 hrs. |
| Petroleum Jelly | 234 ± 30 | 275 ± 67 |
| Nivea Creme ® | 62 ± 12 | 155 ± 31 |
| Ex. 1 Formulation | 566 ± 50 | 593 ± 77 |

The test results in Table IV clearly show that it takes two to three times as long for water to wet paper coated with the stick formulation of Example 1 than it does for water to wet paper treated with either pure petroleum jelly or a commercial occlusive emulsion product. Thus, the stick formulations of the present invention display superior occlusive barrier properties.

EXAMPLE 12

This example demonstrates the stability of the stick formulations prepared in Examples 3 and 5 to syneresis (i.e., separation of liquid from the solid matrix) and drying out.

A sample of about 13 grams was cut from the top portion of the sticks prepared in Examples 3 and 5. Each sample was placed in a tared aluminum weigh pan. The sample in the weigh pan was placed in a controlled humidity oven at 37° C. and 75% relative humidity for a 24 hour period then removed and reweighed. This was repeated three times with a 24 hour period between each heating cycle. Each stick sample was examined for evidence of syneresis after each heating cycle. The weights of the stick samples measured after each heating cycle are summarized in Table V.

After the third heating cycle, the bottom edge of the fragrance stick (Example 5) had melted slightly and flowed onto the surface of the pan, otherwise, no change in appearance of the sticks was observed after three cycles in the humidity oven. Example 5, a formulation containing 8% by weight of fragrance oil lost approximately 1% of its weight.

TABLE V

| | Weights of Stick Samples After Heating at 37°, 75% Relative Humidity | |
|---|---|---|
| Cycle | Example 3 (gms) | Example 5 (gms) |
| Initial | 13.52 | 13.83 |
| 1st | 13.52 | 13.78 |
| 2nd | 13.52 | 13.73 |
| 3rd | 13.52 | 13.69 |

The results in Table V clearly show that the liquid component of the stick formulations of the present invention does not separate out of the solid matrix, and as a result, the stick formulations do not dry out.

Many variations will suggest themselves to those skilled in this art in light of the above detailed description. All such obvious modifications are within the full intended scope of the appended claims.

What is claimed is:

1. An anhydrous delivery vehicle for applying cosmetic or pharmaceutically active ingredients to human skin, said anhydrous delivery vehicle consisting essentially of a blend of:

(A) 5 to 30 weight percent of a wax having a melting point of greater than 100° C. and a weight average molecular weight of less than 10,000;

(B) 5 to 30 weight percent of an acetylated monoglyceride;

(C) 15 to 35 weight percent petrolatum having a specific gravity between 0.815 and 0.880 at 60° C., and a melting range between 38° C. and 60° C.;

(D) 0.1 to 30 weight percent of a fatty alcohol having 8 to 22 carbon atoms; and (E) 0.05 to 50 weight percent of a cosmetically or pharmaceutically active material selected from the group consisting of emollients, sunscreens, vitamins, humectants, botanicals, insect repellents, skin protectants, antiperspirants, bactericides, antiseptics, moisturizers, antioxidants, buffers, pigments, colorants, dyes, fragrances, titanium dioxide, talc, and combinations thereof;

said anhydrous delivery vehicle having superior occlusive barrier properties compared with petroleum jelly alone.

2. An anhydrous formulation for applying cosmetic or pharmaceutically active ingredients to skin, comprising:

5 to 30 weight percent of a wax having a melting point of greater than 100° C. and a weight average molecular weight of less than 10,000;

5 to 30 weight percent of an acetylated monoglyceride;

15 to 35 weight percent of white, amber, or red petrolatum;

0.1 to 30 weight percent of a fatty alcohol having 8 to 22 carbon atoms; and 0.05 to 50 weight percent of a cosmetically or pharmaceutically active material selected from the group consisting of emollients, sunscreens, vitamins, humectants, botanicals, insect repellents, skin protectants, antiperspirants, bactericides, antiseptics, moisturizers, antioxidants, buffers, pigments, colorants, dyes, fragrances, titanium dioxide, talc, and combinations thereof.

3. The anhydrous formulation according to claim 2, containing vitamin E and ascorbyl palmitate.

4. The anhydrous formulation according to claim 2, wherein the wax is a synthetic polyethylene wax.

5. The anhydrous formulation according to claim 2, said anhydrous formulation having superior occlusive barrier properties compared with petroleum jelly alone.

* * * * *